United States Patent [19]

Sheppard et al.

[11] Patent Number: 5,643,922
[45] Date of Patent: Jul. 1, 1997

[54] INDOLE CYCLOHEXYL PLATELET ACTIVATING FACTOR ANTAGONISTS

[75] Inventors: George S. Sheppard, Wilmette; Steven K. Davidsen; James B. Summers, both of Libertyville, all of Ill.

[73] Assignee: Abbott Laboratories, Abbott Park, Ill.

[21] Appl. No.: 677,462

[22] Filed: Jul. 2, 1996

Related U.S. Application Data

[63] Continuation-in-part of Ser. No. 424,911, Apr. 19, 1995, Pat. No. 5,567,711.
[51] Int. Cl.$^6$ ............... C07D 471/02; A61K 31/44
[52] U.S. Cl. ............... 514/303; 514/228.5; 514/234.2; 514/256; 544/62; 544/127; 544/333; 546/118
[58] Field of Search ............... 514/303, 228.5, 514/234.2, 256; 546/118; 544/62, 127, 333

[56] References Cited

U.S. PATENT DOCUMENTS

| | | | |
|---|---|---|---|
| 5,180,723 | 1/1993 | Whittaker et al. | 514/234 |
| 5,180,724 | 1/1993 | Bowles et al. | 514/248 |
| 5,459,152 | 10/1995 | Summers et al. | 514/338 |
| 5,486,525 | 1/1996 | Summers, Jr. et al. | 514/303 |

FOREIGN PATENT DOCUMENTS

| | | |
|---|---|---|
| 9214734 | 1/1992 | WIPO. |
| 9301813 | 2/1993 | WIPO. |
| 9314072 | 7/1993 | WIPO. |
| 9516687 | 6/1995 | WIPO. |

*Primary Examiner*—Joseph McKane
*Assistant Examiner*—Richard S. Myers, Jr.
*Attorney, Agent, or Firm*—Michael P. Martin; Monte R. Browder

[57] ABSTRACT

The present invention provides compounds of formula

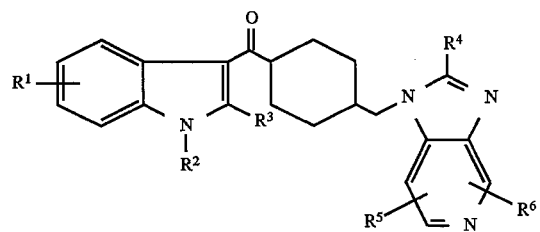

and the pharmaceutically acceptable salts thereof which are potent antagonists of PAF and are useful in the treatment of PAF-related disorders including asthma, rhinitis, shock, respiratory distress syndrome, acute inflammation, transplanted organ rejection, gastrointestinal ulceration, allergic skin diseases, delayed cellular immunity, parturition, fetal lung maturation, and cellular differentiation.

7 Claims, No Drawings

INDOLE CYCLOHEXYL PLATELET ACTIVATING FACTOR ANTAGONISTS

CROSS REFERENCE TO RELATED APPLICATIONS

This is a continuation in part of U.S. Ser. No. 08/424,911 filed Apr. 19, 1995, now issued U.S. Pat. No 5,567,711.

TECHNICAL FIELD

This invention relates to compounds having pharmacological activity, to compositions containing these compounds, and to a medical method of treatment employing the compounds and compositions. More particularly, this invention concerns certain indole cyclohexyl derivatives and their salts which have platelet activating factor (PAF) antagonist activity, to pharmaceutical compositions containing these compounds, and to a method of treating PAF-mediated disorders.

BACKGROUND OF THE INVENTION

Platelet activating factor (PAF) is a phospholipid released from human and other animal cells and is an acetylglyceryl ether of phosphorylcholine as represented by the following formula:

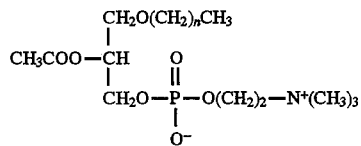

where n is 15 or 17.

PAF is physiologically active and causes contraction of the airway smooth muscle, increased vascular permeability, platelet aggregation, hypotension, and the like. It is now recognized as a powerful mediator of inflammation and may play a physiological or pathobiological role in a variety of clinical conditions, such as asthma and pulmonary dysfunction, rhinitis, acute inflammation, transplanted organ rejection, shock, thrombosis, anaphylaxis, gastrointestinal ulceration, allergic skin diseases, retinal and corneal diseases, chemically induced liver cirrhosis, and ovimplantation in pregnancy. Accordingly, compounds possessing PAF antagonistic effects should be of value in the treatment of any of the above conditions.

SUMMARY OF THE INVENTION

The present invention provides, in its principal aspect, compounds having PAF antagonist activity of formula I:

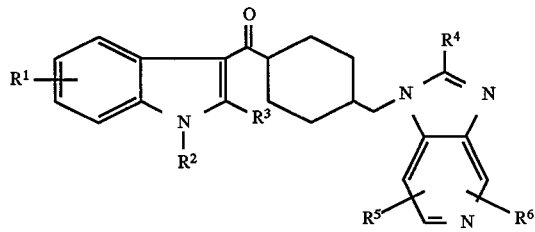

or a pharmaceutically acceptable salt meteor wherein $R^1$ is one or more groups independently selected from the group consisting of (a) hydrogen, (b) halogen, (c) hydroxy, (d) cyano, (e) alkyl of one to six carbon atoms, (f) alkenyl or two to six carbon atoms, (g) alkynyl of two to six carbon atoms, (h) alkoxy of one to six carbon atoms, (i) alkanoyl of one to seven carbon atoms, (j) —COOR$^7$, wherein R$^7$ is hydrogen, alkyl or one to ten carbon atoms, or phenylalkyl wherein the alkyl portion is of one to four carbon atoms, (k) unsubstituted phenyl, (l) phenyl, substituted with alkyl of one to six carbon atoms, alkoxy of one to six carbon atoms, halogen, —NR$^8$R$^9$, where R$^8$ and R$^9$ are independently selected from hydrogen and alkyl of one to six carbon atoms, or R$^8$ and R$^9$ together with the nitrogen atom to which they are attached form a pyrrolidinyl, piperidinyl, piperazinyl, or morpholinyl ring, —COOR$^7$, —C(O)NR$^8$R$^9$, or —SO$_2$NR$^8$R$^9$, (m) —C(O)NR$^8$R$^9$, (n) —OC(O)NR$^8$R$^9$, (o) —NHC(O)NR$^8$R$^9$, (p) 2- or 3-furyl, (q) 2- or 3-thienyl, (r) 2-, 4-, or 5-thiazolyl, (s) 2-, 3-, or 4-pyridyl, (t) 2-, or 4-pyrimidyl, (u) phenylalkyl in which the alkyl portion is one one to six carbon atoms, (v) phenylalkyl, in which the alkyl portion is of one to six carbon atoms and the phenyl moiety is substituted with halogen, alkyl of from one to six carbon atoms, or alkoxy of from one to six carbon atoms, (w) unsubstituted benzoyl, (x) benzoyl substituted with halogen, alkyl of from one to six carbon atoms, or alkoxy of from one to six carbon atoms, (y) unsubstituted phenoxy, (z) phenoxy substituted with halogen, alkyl of from one to six carbon atoms, or alkoxy of from one to six carbon atoms, (aa) unsubstituted phenylalkyloxy, in which the alkyl portion is of one to six carbon atoms, (bb) phenylalkyloxy in which the alkyl portion is of one to six carbon atoms and the phenyl moiety is substituted with halogen, alkyl of from one to six carbon atoms, or alkoxy of from one to six carbon atoms, (cc) unsubstituted phenylalkanoyl, in which the alkanoyl portion is of one to seven carbon atoms, and (dd) phenylalkoyl, in which the alkanoyl portion is of one to seven carbon atoms and the phenyl moiety is substituted with halogen, alkyl of from one to six carbon atoms, or alkoxy of from one to six carbon atoms.

$R^2$ is selected from the group consisting of (a) hydrogen, (b) alkyl of one to six carbon atoms, (c) —(CH$_2$)$_p$COOR$^7$, where p is 0, 1, 2, 3, or 4, (d) —(CH$_2$)$_q$NR$^8$R$^9$, where q is 2, 3, or 4, (e) —(CH$_2$)$_p$COR$^7$, (f) —(CH$_2$)$_q$OR$^7$, (g) —(CH$_2$)$_p$SO$_2$R$^7$, (h) (CH$_2$)$_p$SO$_2$NR$^8$R$^9$, (i) —(CH$_2$)$_p$CONR$^{10}$R$^{11}$, where R$^{10}$ and R$^{11}$ are independently selected from the group consisting of hydrogen, alkyl of one to six carbon atoms, —(CH$_2$)$_r$COOR$^7$, where r is 1, 2, 3, or 4, —(CH$_2$)$_r$NR$^8$R$^9$, —(CH$_2$)$_r$OR$^7$, —(CH$_2$)$_r$SO$_2$R$^7$, and —(CH$_2$)$_r$SO$_2$NR$^8$R$^9$, or R$^{10}$ and R$^{11}$ taken together define a pyrrolidine, morpholine, or thiomorpholine ring, (j) —(CH$_2$)$_p$CN, (k) —(CH$_2$)$_p$-1H-tetrazol-5-yl, (l) —CONHNH$_2$, (m) unsubstituted phenylalkyl wherein the alkyl portion is of one to four carbon atoms, and (n) phenylakyl wherein the alkyl portion is of one to four carbon atoms and the phenyl moiety is substituted with halogen, alkyl of from one to six carbon atoms, or alkoxy of from one to six carbon atoms.

$R^3$ is selected from the group consisting of hydrogen and alkyl of one to six carbon atoms.

$R^4$ is selected from the group consisting of (a) alkyl of one to six carbon atoms, (b) alkenyl of two to six carbon atoms, (c) alkynyl of two to six carbon atoms, (d) alkoxy of one to six carbon atoms, (e) alkylthio of one to six carbon atoms, (f) alkoxyalkyl in which the alkoxy and alkyl portions are independently of one to six carbon atoms, (g) alkylthioalkyl in which the alkyl portions each independently of one to six carbon atoms, (h) haloalkyl of one to six carbon atoms, (i) unsubstituted phenylalkyl wherein the alkyl portion is of one to six carbon atoms, (j) phenylalkyl wherein the alkyl portion io of one to six carbon atoms and the phenyl is substituted with alkyl of one to six carbon atoms, haloalkyl of one to six carbon atoms, alkoxy of one to six carbon atoms, hydroxy, or halogen, (k) cycloalkyl of three to eight carbon atoms, (l) unsubstituted thiophenyl, and (m) thiophenyl substituted with alkyl of one to six carbon atoms, haloalkyl of one to six carbon atoms, alkoxy of one to six carbon atoms, hydroxy, or halogen.

$R^5$ and $R^6$ are independently selected from the group consisting of hydrogen, alkyl of one to six carbon atoms, halogen, haloalkyl, and alkoxy of one to six carbon atoms.

Compounds of the present invention may exhibit stereoisomerism by virtue of the presence of one or more asymmetric or chiral centers in the compounds. The present invention contemplates the various stereoisomers and mixtures thereof. Desired enantiomers are obtained by chiral synthesis from commercially available chiral starting materials by methods well known in the art, or may be obtained from mixtures of the enantiomers by resolution using known techniques.

In another aspect, the present invention provides pharmaceutical compositions useful for the treatment of PAF-mediated disorders comprising a therapeutically effective amount of a compound of formula I above in combination with a pharmaceutically acceptable carrier.

In another aspect, the present invention provides a method of inhibiting PAF activity by administering to a host mammal in need of such treatment an effective amount of a PAF-inhibiting compound having structure I above.

In yet another aspect of the present invention, there is provided a method of treating PAF-mediated disorders including asthma, rhinitis, shock, respiratory distress syndrome, acute inflammation, delayed cellular immunity, parturition, fetal lung maturation, and cellular differentiation by administering to a host mammal in need of such treatment a therapeutically effective amount of a compound of structure I above.

DETAILED DESCRIPTION OF THE INVENTION

Definitions of Terms

As used throughout this specification and the appended claims, the following terms have the meanings specified.

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkylthio" refers to an alkyl group, as defined above, attached to the parent molecular moiety through a sulfur atom and includes such examples as methylthio, ethylthio, propylthio, n-, sec- and tert-butylthio and the like.

The term "alkylthioalkyl" refers to an alkylthio group, as defined above, attached to the parent molecular moiety through an alkylene group and includes such examples as methylthiomethyl, ethylthiomethyl, propylthiomethyl, n-, sec- and tert-butylthiomethyl and the like.

The term "alkanoyl" represents an alkyl group, as defined above, attached to the parent molecular moiety through a carbonyl group. Alkanoyl groups are exemplified by formyl, acetyl, propionyl, butanoyl and the like.

The terms "alkoxy" or "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkyl" refers to an alkoxy group, as defined above, attached through an alkylene group to the parent molecular moiety. Representative alkoxyalkyl groups include methoxymethyl, methoxyethyl, ethoxyethyl, and the like.

The term "alkoxycarbonyl" represents an ester group; i.e. an alkoxy group attached to the parent molecular moiety through a carbonyl group. Representative examples include methoxycarbonyl, ethoxycarbonyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocarbon containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "alkynylene" refers to a divalent group derived by the removal of two hydrogen atoms from a straight or branched chain acyclic hydrocarbon group containing a carbon-carbon triple bond. Examples of alkynylene include

—C≡CH—, —C≡CH—CH$_2$—, —C≡CH—CH(CH$_3$)—, and the like.

The term "cycloalkyl" denotes a monovalent group derived from a monocyclic or bicyclic saturated carbocyclic ring compound by the removal of a single hydrogen atom. Examples include cyclopropyl, cyclobutyl, cyclopentyl, cyclohexyl, bicyclo[2.2.1]heptanyl, and bicyclo[2.2.2]octanyl.

The term "cycloalkylene" refers to a divalent group derived from a saturated carbocyclic hydrocarbon by the removal of two hydrogen atoms, for example cyclopentylene, cyclohexylene, and the like.

The term "haloalkyl" denotes an alkyl group, as defined above, having one, two, or three halogen atoms attached thereto and is exemplified by such groups as chloromethyl, bromoethyl, trifluoromethyl, and the like.

The term "phenoxy" refers to a phenyl group attached to the parent molecular moiety through an oxygen atom.

The term "phenylalkyloxy" refers to a pheny group attached to the parent molecular moiety through an alkylene group and thence through an oxygen atom. Representative phenylalkyloxy groups include phenylmethoxy, phenylethy-2-yloxy, phenylprop-3-yloxy, phenylprop-2-yloxy, and the like.

The term "phenylalkanoyl" as used herein refers to a pheny group attached to the parent molecular moiety through an alkyl group and thence through a carbonyl group.

The term "thiophenyl" refers to a phenyl group attached to the parent molecular moiety through a sulfur atom.

By "pharmaceutically acceptable salt" it is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in *J. Pharmaceutical Sciences*, 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The terms "PAF-related disorders" and "PAF-mediated disorders" are used herein to mean disorders related to PAF or mediated by PAF, including asthma, rhinitis, shock, respiratory distress syndromes, acute inflammation, gastric ulceration, transplant organ rejection, psoriasis, allergic skin disease, ischemia and reperfusion injury, delayed cellular immunity, parturition, fetal lung maturation, and cellular differentiation.

Preferred Embodiments

In a preferred embodiment, the compounds of this invention are represented by formula I wherein $R^1$ is one or more groups independently selected from the group consisting of (a) hydrogen, (b) halogen, (c) alkyl of one to six carbon atoms, (d) alkynyl of two to four carbon atoms, (e) alkoxy of one to six carbon atoms, (f) phenyl, optionally substituted with alkyl of one to six carbon atoms, alkoxy of one to six carbon atoms, or halogen, (f) —COOR$^7$, wherein $R^7$ is hydrogen, alkyl of one to ten carbon atoms, or phenylalkyl wherein the alkyl portion is of one to four carbon atoms, (g) —C(O)NR$^8$R$^9$, (h) —OC(O)NR$^8$R$^9$, (i) 2- or 3-furyl, and (j) 2- or 3-thienyl; $R^2$ is defined above; $R^3$, $R^5$, and $R^6$ are hydrogen; and $R^4$ is alkyl of one to six carbon atoms.

In a more preferred embodiment, the compounds of this invention are represented by formula I wherein $R^2$ is selected from the group consisting of (a) —CONR$^{10}$R$^{11}$, where $R^{10}$ and $R^{11}$ are independently selected from hydrogen and alkyl of one to six carbon atoms, and (b) —(CH$_2$)$_q$OR$^7$, wherein q is 2, 3, or 4, and $R^7$ is alkyl of one to four carbon atoms; and $R^1$, $R^3$, $R^4$, $R^5$, and $R^6$ are defined immediately above.

Compounds representative of this embodiment include, but are not limited to:

3-{[trans-4-[(1H-2-methylimidazo[4.5-c]pyrid-1-yl) methylcyclohex-1-yl]carbonyl}indole-1,4-dicarboxylic acid 1-dimethyl amide 4-methyl ester hydrochloride, 6-(4-fluorophenyl)-3-{[trans-4-[(1H-2-methylimidazo[4.5-c]pyrid-1-yl)methylcylohex-1-]carbonyl}indole-1 carboxylic acid dimethyl amide hydrochloride, 6-(4-fluorophenoxy)-3- {[trans-4-[(1H-2-methylimidazo[4.5-c]pyrid-1-yl)methylcyclohex-1-yl] carbonyl}indole-1 carboxylic acid dimethyl amide hydrochloride, 6-phenylmethyl-3-{[trans-4-[(1H-2-methylimidazo[4.5-c]pyrid-1-yl)methylcyclohex-1-yl]carbonyl}indole-1 carboxylic acid dimethyl amide hydrochloride, 6-(4-methoxyphenyl)-3-{[trans-4-[(1H-2-methylimidazo[4.5-c]pyrid-1-yl)methylcyclohex-1-yl] carbonyl}indole-1 carboxylic acid dimethyl amide hydrochloride, 6-(pyrid-3-yl)-3-{[trans-4-[(1H-2-methylimidazo[4.5-c]pyrid-1-yl)methylcyclohex-1-yl]carbonyl}indole-1 carboxylic acid dimethyl amide hydrochloride, 5-methoxy-3-{[trans-4-[(1H-2-methylimidazo[4.5-c]pyrid-1-yl)methylcyclohex-1-yl]carbonyl}indole-1 carboxylic acid dimethyl amide hydrochloride, 4-methyl-3-{[trans-4-[(1H-2-methylimidazo[4.5-c]pyrid-1-yl)methylcyclohex-1-yl]carbonyl}indole-1 carboxylic acid dimethyl amide hydrochloride, 4-ethynyl-3-{[trans-4-[(1H-2-methylimidazo[4.5-c]pyrid-1-yl) methylcyclohex-1-yl]carbonyl}indole-1 carboxylic acid dimethyl amide hydrochloride, 4-(fur-2-yl)-3-{[trans-4-[(1H-2-methylimidazo[4.5-c]pyrid-1-yl)methylcyclohex-1-yl]carbonyl}indole-1 carboxylic acid dimethyl amide hydrochloride, 4-(thien-2-yl)-3-{[trans-4-[(1H-2-methylimidazo[4.5-c] pyrid-1-yl)methylcyclohex-1-yl]carbonyl}indole-1 carboxylic acid dimethyl amide hydrochloride, 4-hydroxy-3-{[trans-4-[(1H-2-methylimidazo[4.5-c]pyrid-1-yl)methylcyclohex-1-yl]carbonyl}indole-1 carboxylic acid dimethyl amide hydrochloride.

4-(N,N-dimethylaminocarbonyloxy)-3-{[trans-4-[(1H-2-methylimidazo[4.5-c]pyrid-1-yl)methylcyclohex-1-yl] carbonyl}indole-1 carboxylic acid dimethyl amide hydrochloride, 4-chloro-3-{[trans-4-[(1H-2-methylimidazo[4.5-c]pyrid-1-yl)methylcyclohex-1-yl]carbonyl}indole-1 carboxylic acid dimethyl amide hydrochloride, and 1-(2-ethoxyethyl)-6-(4-fluorophenyl)-3-{[trans-4-[(1H-2-methylimidazo[4.5-c]pyrid-1-yl)methylcyclohex-1yl] carbonyl}indole hydrochloride.

The most preferred compound of the present invention is 3-{[trans-4-[(1H-2-methylimidazo[4.5-c]pyrid-1-yl) methylcyclohex-1-yl]carbonyl}indole-1,4-dicarboxylic acid 1-dimethyl amide 4-methyl ester hydrochloride.

PAF Inhibitory Activity of the Compounds of the Present Invention

The ability of representative compounds of the present invention to inhibit PAF activity was determined in an in vitro test using the following method.

Citrated whole rabbit blood was obtained from Pel-Freez (Rogers, A R). Rabbit platelets were prepared by centrifugation and washing. The platelets were lysed by freeze-thawing and sonication; platelet membranes were prepared by centrifugation and washing. Final membrane preparations were stored frozen in 10 mM Tris/5 mM MgCl$_2$/2 mM EDTA (TME buffer, pH 7.0) with 0.25M sucrose added for membrane stabilization.

The standard PAF receptor binding assay contained 10 μg platelet membrane protein, 0.6 nM [$^3$H]C$_{18}$-PAF (from Amersham or New England Nuclear; specific activity 120–180 Ci/mmol), with and without test compound, in "binding buffer" consisting of TME with 0.25% bovine serum albumin added (Sigma, RIA grade). The final volume of the assay was 100 μl. The assay was conducted in Millititre-GV™ (Millipore Corp.) filtration plates; incubation time was for 60 minutes at room temperature (22°–23° C.). "Specific binding" was operationally defined as the arithmetic difference between "total binding" of 0.6 nM [$^3$H]C$_{18}$-PAF (in the absence of added PAF) and "nonspecific binding" (in the presence of 1 μM PAF). After the prescribed incubation, platelet membranes were filtered under vacuum and washed with 1 milliliter of "binding buffer". The filters were dried and removed. The bound radioactivity was quantitated with a Berthold TLC-Linear Analyzer model LB2842.

Dose-response curves of inhibition of specific $[^3H]C_{18}$-PAF binding by test compounds were conducted in triplicate, with at least four doses covering the active range. Experiments were repeated at least once. $IC_{50}$ values (concentration producing 50% inhibition) were determined by point-to-point evaluation. $K_i$ values of inhibitory binding constants were calculated according to the method of Cheng and Prusoff [*Biochem. Pharmacol.* 22 (1973) 3099–3108] whereby $$K_i = \frac{IC_{50}}{1+([[^3H]PAF]/K_d[^3H]PAF)}$$
$$= \frac{IC_{50}}{1+(0.6\,nM/0.6\,nM)}$$
$$= \frac{IC_{50}}{2}$$

The compounds of the present invention inhibit PAF activity as indicated for 3-{[trans-4-[(1H-2-methylimidazo[4.5-c]pyrid-1-yl)methylcyclohex-1-yl]carbonyl}indole-1,4-dicarboxylic acid 1-dimethyl amide 4-methyl ester hydrochloride (Example 1) which has a $K_i$ of 2.4 nM.

Pharmaceutical Compositions

The present invention also provides pharmaceutical compositions which comprise one or more of the compounds of formula I above formulated together with one or more non-toxic pharmaceutically acceptable carders. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracistemally, intravaginally, intraperitoneally, topically (as by powders, ointments, or drops), butally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions, or emulsions as well as sterile powders for reconstitution into sterile injectable solutions or dispersions just prior to use. Examples of suitable aqueous and non-aqueous carriers, diluents, solvents, or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Compositions for rectal or vaginal administration are preferably suppositories which can be prepared by mixing the compounds of this invention with suitable non-irritating excipients or carders such as cocoa butter, polyethylene glycol, or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments, and inhalants. The active compound is mixed under sterile conditions with a pharmaceutically acceptable carrier and any needed preservatives, buffers, or propellants which may be required.

Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved.

Generally dosage levels of about 0.001 to about 100 mg, more preferably of about 0.01 to about 20 mg, and most preferably about 0.1 to about 10 mg of active compound per kilogram of body weight per day are administered orally to a mammalian patient. If desired, the effective daily dose may be divided into multiple doses for purposes of administration, e.g. two to four separate doses per day.

Preparation of Compounds of the Invention

The compounds of this invention may be prepared as outlined in Scheme 1. Reaction of Indole 1 with ethylmagnesium bromide, $ZnCl_2$, and acid chloride 2, gives 3-acylindole 3. The group $R^2$ is then introduced by reaction of 3 with a base such as NaH or KOH and $R^2X$ or $(R_2)_2O$ wherein $R^2$ is defined above, X is a suitable leaving group such as Cl, Br, I, methanesulfonyl, trifluoromethanesulfonyl, p-toluenesulfonyl, and the like to give 4. Removal of the benzyloxycarbonyl group, for example using $H_2$ and Palladium on carbon, followed by condensation of the primary amine 5 with 3-nitro-4-ethoxypyridine gives 6. Reduction of the nitro group using $SnCl_2$, or preferably $H_2$ and Palladium on carbon, gives diamine 7 which is converted to the desired compound 8 by reaction with $(R^4CO)_2O$ and $R^4CO_2H$ where $R^4$ is alkyl or haloalkyl; $R^4COCl$ where $R^4$ is aryl; or ethyl(ethoxymethylene)cyanoacetate where $R^4$ is H.

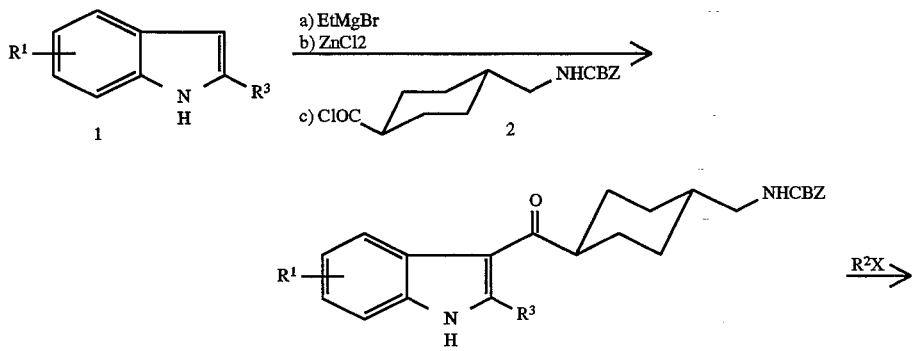

Scheme 1

-continued
Scheme 1

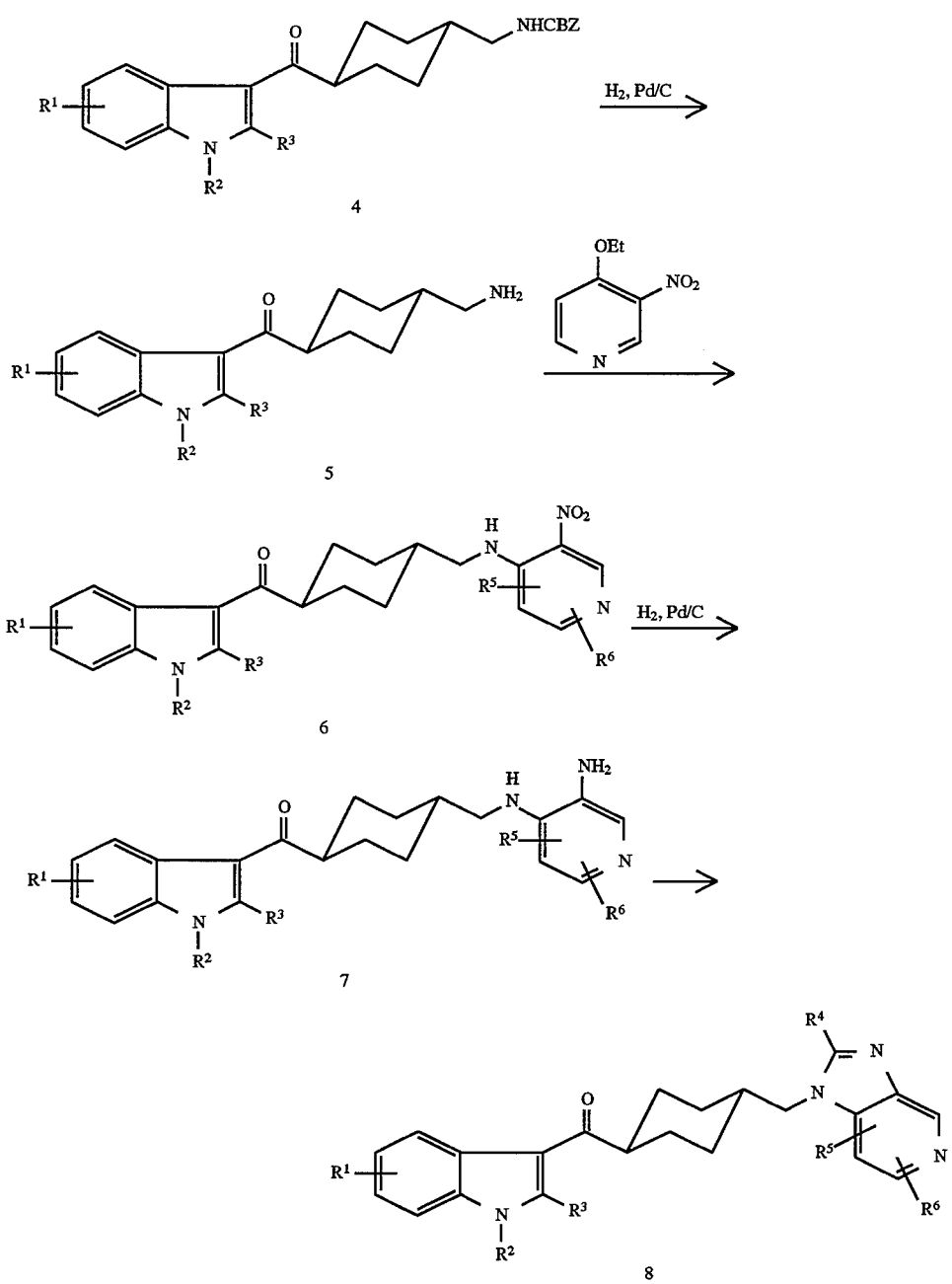

The foregoing may be better understood by the following Examples, which are presented for illustration and are not intended to limit the scope of the invention.

EXAMPLE 1

Preparation of 3-{[trans-4-[(1H-2-methylimidazo [4,5-c]pyrid-1-yl)methylcyclohex-1-yl] carbonyl}indole-1,4-dicarboxylic acid 1-dimethyl amide 4-methyl ester hydrochloride Step 1: trans-4-(N-carbobenzyloxy)aminomethyl-1-cyclohexane carboxylic acid To a 0° C. solution of trans-4-aminomethyl-1-cyclohexane carboxylic acid (6.28 g, 0.04 mol) in 10% aqueous NaOH (16 mL) was added dropwise benzyl chloroformate (8.29 g, 0.049 mol) and 10% aqueous NaOH (20 mL). The cold bath was removed and the reaction mixture was stirred vigorously for one hour. The thick white paste was shaken with aqueous 1M HCl (100 mL) and the white solid was isolated by filtration, washed with $H_2O$, and dried overnight in vacuo to give trans-4-(N-carbobenzyloxy) aminomethyl-1-cyclohexane carboxylic acid.

Step 2: trans-4-(N-carbobenzyloxy)aminomethyl-1-cyclohexane carbonyl chloride

A mixture of trans-4-(N-carbobenzyloxy)aminomethyl-1-cyclohexane carboxylic acid (5.02 g, 17.3 mmol), prepared as in step 1, and thionyl chloride was heated at 40° C. for 30 minutes. The reaction mixture was cooled to ambient temperature and diluted with pentane (50 mL). Trans-4-(N-carbobenzyloxy)aminomethyl-l-cyclohexane carbonyl chloride (4.37 g) was isolated by filtration and drying in vacuo.

Step 3: 3-[(trans-1-(N-carbobenzyloxy) aminomethylcyclohex-4-yl)carbonyl]indole-4-carboxylic acid methyl ester To a solution of indole-4-carboxylic acid methyl ester (2.33 g, 13.3 mmol) in $CH_2Cl_2$ (25 mL) was added ethylmagnesium bromide (3M in ether, 4.4 mL, 13.2 mmol). The reaction mixture was stirred for five minutes and $ZnCl_2$ (1M in ether, 40 mL, 40 mmol) was added and the cloudy, brown suspension was stirred for 15 minutes. A solution of trans-4-(N-carbobenzyloxy)aminomethyl-1-cyclohexane carbonyl chloride (4.36 g, 14.1 mmol), prepared as in step 2, in $CH_2Cl_2$ (20 mL) was added and the reaction mixture was stirred for three hours. The reaction mixture was poured into a separatory funnel containing saturated aqueous $NH_4Cl$ which left a green-brown gum. The gum was broken up by trituration with aqueous 1M HCl and $CH_2Cl_2$/methanol and added to the separatory funnel. The layers were separated and the organic phase was washed with saturated aqueous $NaHCO_3$, dried over $MgSO_4$, filtered, and concentrated in vacuo. Chromatography on silica gel (1%, then 3% methanol/$CH_2Cl_2$) gave 3-[(trans-4-(N-carbobenzyloxy) aminomethylcyclohex-1-yl)carbonyl]indole-4-carboxylic acid methyl ester (2.83 g, 48%) as a tan foam.

Step 4: 3-[(trans-1-(N-carbobenzyloxy) aminomethylcyclohex-4-yl)carbonyl]indole-1,4-dicarboxylic acid 1-dimethyl amide 4-methyl ester The desired compound was prepared by treatment of a solution in THF of 3-[(trans-4-(N-carbobenzyloxy) aminomethylcyclohex-1-yl)carbonyl]indole-4-carboxylic acid methyl ester, prepared as in step 3, with powdered KOH (5.0 equiv.) and dimethylcarbamyl chloride (2.0 equiv.).

Step 5: 3-[(trans-1-aminomethylcyclohex-4-yl) carbonyl]indole-1,4-dicarboxylic acid 1-dimethyl amide 4-methyl ester The desired compound was prepared by catalytic hydrogenation (10% Pd/C, 4 atm $H_2$, ethanol, 17 hours) of 3-[(trans-1-(N-carbobenzyloxy)aminomethylcyclohex-4-yl) carbonyl]indole-1,4-dicarboxylic acid 1-dimethyl amide 4-methyl ester.

Step 6: 3-[(trans-1-(N-3-nitropyrid-3-yl) aminomethylcyclohex-4-yl)carbonyl]indole-1,4-dicarboxylic acid 1-dimethyl amide 4-methyl ester A mixture of 3-[(trans-1-aminomethylcyclohex-4-yl) carbonyl]indole-1,4-dicarboxylic acid 1-dimethyl amide 4-methyl ester (1.04 g, 2.70 mmol), prepared as in step 5, and 4-ethoxy-3-nitropyridine (0.485 g, 2.89 mmol) in $CH_3CN$ (10 mL) was heated at reflux for 40 hours, then at 100° C. for an amount of time sufficient to distill off the solvent. The residue was cooled to ambient temperature and dried under vacuum to give a yellow foam (1.44 g) which was used without further purification.

Step 7: 3-[(trans-1-(3-aminopyrid-4-yl) aminomethylcyclohex-4-yl)carbonyl]indole-1,4-dicarboxylic acid 1-dimethyl amide 4-methyl ester The desired compound was prepared by catalytic hydrogenation (10% Pd/C, 4 atm $H_2$, ethanol, 8 hours) of 3-[(trans-1-(N-3-nitropyrid-3-yl)aminomethylcyclohex-4-yl)carbonyl]indole-1,4-dicarboxylic acid 1-dimethyl amide 4-methyl ester.

Step 8: 3{[trans-4-[(1H-2-methylimidazo[4.5-c] pyrid-1-yl)methylcyclohex-1-yl]carbonyl}indole-1,4-dicarboxylic acid 1-dimethyl amide 4-methyl ester hydrochloride A solution of 3-[(trans-1-(3-aminopyrid-4-yl) aminomethylcyclohex-4-yl)carbonyl]indole-1,4-dicarboxylic acid 1-dimethyl amide 4-methyl ester (0.885 g, 1.86 mmol), prepared as in step 7, in acetic anhydride (5 mL) and acetic acid (5 mL) was heated overnight at reflux. The reaction mixture was cooled to ambient temperature and quenched with methanol (25 mL). The solvents were removed in vacuo and the residue partitioned between $CH_2Cl_2$ and saturated aqueous $NaHCO_3$. The organic phase was dried over $MgSO_4$, filtered, and concentrated in vacuo to give a brown foam (0.848 g). Purification by chromatography on silica gel 1%, then 2.5%, then 4%, then 5% methanol/$CH_2Cl_2$) gave 3-{[trans-4-[(1H-2-methylimidazo [4.5-c]pyrid-1-yl)methylcyclohex-1-yl]carbonyl}indole-1,4-dicarboxylic acid 1-dimethyl amide 4-methyl ester (0.278 g) as a brown foam. The foam was dissolved in THF (10 mL) and 4N HCl/dioxane (0.15 mL) was added. The resulting precipitate was filtered, washed with ether, and dried in vacuo to give 3-{[trans-4-[(1H-2-methylimidazo[4.5-c] pyrid-1-yl)methylcyclohex-1-yl]carbonyl}indole-1,4-dicarboxylic acid 1-dimethyl amide 4-methyl ester hydrochloride (0.212 g). $^1$H NMR ($D_3COD$, 300 MHz) δ9.19 (s, 1H), 8.57 (d, 1H), 8.39 (s, 1H), 8.26 (m, 1H), 7.75 (d, 1H), 7.43 (m, 2H), 4.35 (m, 2H), 3.80 (s, 3H), 3.01(s, 6H), 2.82 (s, 3H), 2.81 (m, 1H), 2.02 (m, 2H), 1.77 (m, 1H), 1.48 (m, 4H), 1.24 (m, 2H). MS (DCI/$NH_3$) m/e 502 (m+H)$^+$, 244.

EXAMPLE 2

Preparation of 6-(4-fluorophenyl)-3-{[trans-4-[(1H-2-methylimidazo[4.5-c]pyrid-1yl)methylcyclohex-1-yl]carbonyl}indole-1 carboxylic acid dimethyl amide hydrochloride The desired compound is prepared according to the method of Example 1, except substituting 6-(4-fluorophenyl)indole, prepared as described in International Application Number PCT/US92/05890 (4 Feb. 1993) for indole-4-carboxylic acid methyl ester.

EXAMPLE 3

Preparation of 6-(4-fluorophenoxy)-3-{[trans-4-[ (1H-2-methylimidazo[4.5-c]pyrid-1-yl) methylcyclohex-1-yl]carbonyl}indole-1 carboxylic acid dimethyl amide hydrochloride

Step 1. 2-Nitro-4-(4-fluorophenoxy)toluene

4-Bromo-2-nitrotoluene (25.0g, 116 mmol), 4-fluorophenol (8.70g, 77.6 mmol), potassium carbonate (21.5g, 156 mmol) and pyridine (75 mL), were combined under $N_2$ atmosphere and heated at 90° C. for 30 min. The reaction mixture was cooled to ambient temperature, CuO (15.4g, 194 mmol) was added under a stream of N2, and the resulting dark-brown suspension was heated at reflux for 17 hours. The reaction mixture was cooled to ambient temperature and diluted with ether. The solids were removed by filtration through celite. The ethereal solution was washed with 1.0M aqueous NaOH, 1.0M aqueous HCl and brine, dried over Na$_2$SO$_4$, filtered and concentrated in vacuo to give a dark-brown oil. The crude product was purified by chromatography on silica gel to give 2-nitro-4-(4-fluorophenoxy)-toluene (12.1 g, 63%).

Step 2. E-1-(1-pyrrolidinyl)-2-[2-nitro-4-(4-fluorophenoxy)phenyl]ethylene

2-Nitro-4-(4-fluorophenoxy)toluene (11.8 g, 47.7 mmol), was dissolved in dimethylformamide (90.0 mL) under N$_2$ atmosphere. Dimethylformamide dimethyl acetal (20.2 mL, 143 mmol), and pyrrolidine (4.0 mL, 47.4 mmol) were added via syringe and the reaction mixture was heated at 110° C. for 3 hours. The reaction mixture was cooled to ambient temperature and partitioned between H$_2$O and ether. The organic phase was washed with H$_2$O. The combined aqueous extracts were washed with ether. The ether extracts were combined and dried over Na$_2$SO$_4$, filtered, and concentrated in vacuo to give a viscous oil (16.1 g) which was used without further purification.

Step 3. 6-(4-fluorophenoxy)indole

The material prepared as in step 2 was dissolved in 80% aqueous acetic acid (320 mL, 4540 mmol) and the reaction mixture was warmed to 75° C. Zinc dust (27 g, 413 mmol) was added in 5 portions over 1 hour. The resulting dark-brown suspension was warmed to 90° C. and heated for two hours. The reaction mixture was cooled to ambient temperature and diluted with ether. The solids were removed by filtration through celite. The filter cake was rinsed with H$_2$O and ether. The layers were separated and the organic phase was washed with H$_2$O, with saturated aqueous NaHCO$_3$ until basic, then once with brine, dried over Na$_2$SO$_4$, filtered, and concentrated in vacuo. The crude product was purified by chromatography on silica gel to give 6-(4-fluorophenoxy)-indole (1.8 g, 17%)

Step4: 6-(4fluorophenoxy)-3-{[trans-4-[(1H-2-methylimidazo[4.5-c]pyrid-1-yl)methylcyclohex-1-yl]carbonyl}indole-1 carboxylic acid dim ethyl amide hydrochloride The desired compound is prepared according to the method of Example 1, except substituting 6-(4-fluorophenoxy)indole for indole-4-carboxylic acid methyl ester.

EXAMPLE 4

Preparation of 6-phenylmethyl-3-{[trans-4-[(1H-2-methylimidazo[4.5-c]pyrid-1-yl)methylcyclohex-1-yl]carbonyl}indole-1 carboxylic acid dimethyl amide hydrochloride The desired compound is prepared according to the method of Example 1, except substituting 6-phenylmethylindole for indole-4-carboxylic acid methyl ester.

EXAMPLE 5

Preparation of 6-(4-methoxyphenyl-3-{[trans-4-[(1H-2-methylimidazo[4.5-c]pyrid-1-yl)methylcyclohex-1-yl]carbonyl]indole-1 carboxylic acid dimethyl amide hydrochloride The desired compound is prepared according to the method of Example 1, except substituting 6-(4-methoxyphenyl)indole, prepared as described in WO 93/01813, for indole-4-carboxylic acid methyl ester.

EXAMPLE 6

Preparation of 6-(pyrid-3-yl)-3-{[trans-4-[(1H-2-methylimidazo[4.5-c]pyrid-1-yl)methylcyclohex-1-yl]carbonyl}indole-1 carboxylic acid dimethyl amide hydrochloride The desired compound is prepared according to the method of Example 1, except substituting 6-(pyrid-3-yl) indole, prepared as described in WO 93/01813, for indole-4-carboxylic acid methyl ester.

EXAMPLE 7

Preparation of 5-methoxy-3-{[trans-4-[(1H-2-methylimidazo[4.5-c]pyrid-1-yl)methylcyclohex-1-yl]carbonyl}indole-1 carboxylic acid dimethyl amide hydrochloride The desired compound is prepared according to the method of Example 1, except substituting 5-methoxyindole for indole-4-carboxylic acid methyl ester.

EXAMPLE 8

Preparation of 4-methyl-3-{[trans-4-[(1H-2-methylimidazo[4.5-c]pyrid-1-yl)methylcyclohex-1-yl]carbonyl]indole-1 carboxylic acid dimethyl amide hydrochloride The desired compound is prepared according to the method of Example 1, except substituting 4-methylindole for indole-4-carboxylic acid methyl ester.

EXAMPLE 9

Preparation of 4-ethynyl-3-{[trans-4-[(1H-2-methylimidazo[4.5-c]pyrid-1-yl)methylcyclohex-1-yl]carbonyl}indole-1 carboxylic acid dimethyl amide hydrochloride Step 1: 4-bromo-3-{[trans-4-[(1H-2-methylimidazo [4.5-c]pyrid-1-yl)methylcyclohex-1-yl] carbonyl}indole-1 carboxylic acid dimethyl amide The desired compound is prepared according to the method of Example 1, except substituting 4-bromoindole for indole-4-carboxylic acid methyl ester.

Step 2: 4-(trimethylsilylethynyl)-3-{[trans-4-[(1H-2-methylimidazo[4.5-c]pyrid-1-yl)methylcyclohex-1-yl]carbonyl}indole-1 carboxylic acid dimethyl amide The desired compound is prepared by heating a mixture of (trimethylsilylethynyl)stannane, 4-bromo-3-{[trans-4-[(1H-2-methylimidazo[4.5-c]pyrid-1-yl)methylcyclohex-1-yl] carbonyl}indole-1 carboxylic acid dimethyl amide, tetrakis (triphenylphosphine)palladium(0), and toluene in a pressure bottle at 120° C. for an amount of time sufficient to consume substantially all of the starting indole.

Step 3: 4-ethynyl-3-{[trans-4-[(1H-2-methylimidazo [4.5-c]pyrid-1-yl)methylcyclohex-1-yl] carbonyl}indole-1 carboxylic acid dimethyl amide hydrochloride The desired compound is prepared by treating a solution in THF/CH$_3$CN of 4-(trimethylsilylethynyl)-3-{[trans-4-[(1H-2-methylimidazo[4.5-c]pyrid-1-yl)methylcyclohexyl] carbonyl}indole-1 carboxylic acid dimethyl amide, prepared

17 as in step 2, with CsF at ambient temperature. Treatment with HCl/dioxane as described in Example 1, step 8, provides the hydrochloride salt.

EXAMPLE 10

Preparation of 4-(fur-2-yl)-3-{trans-4-[(1H-2-methylimidazo[4.5-c]pyrid-1-yl)methylcyclohex-1-yl]carbonyl}indole-1 carboxylic acid dimethyl amide hydrochloride The desired compound is prepared according to the method of Example 9, steps 1, 2, 4, and 5, except substituting tri(n-butyl)-(fur-2-yl)stannane for (trimethylsilylethynyl)stannane.

EXAMPLE 11

Preparation of 4-(thien-2-yl)-3-{[trans-4-[(1H-2-methylimidazo[4.5-c]pyrid-1-yl)methylcyclohex-1-yl]carbonyl}indole-1 carboxylic acid dimethyl amide hydrochloride The desired compound is prepared according to the method of Example 9, steps 1, 2, 4, and 5, except substituting tri(n-butyl)-(thien-2-yl)stannane for (trimethylsilylethynyl)stannane.

EXAMPLE 12

Preparation of 4-hydroxy-3-{[trans-4-[(1H-2-methylimidazo[4.5-c]pyrid-1-yl)methylcyclohex-1-yl]carbonyl}indole-1 carboxylic acid dimethyl amide hydrochloride Step 1: 4-methoxy-3-{[trans-4-[(1H-2-methylimidazo[4.5-c]pyrid-1-yl)methylcyclohex-1-yl]carbonyl}indole-1 carboxylic acid dimethyl amide The desired compound is prepared according to the method of Example 1, except substituting 4-methoxyindole for indole-4-carboxylic acid methyl ester.

Step 2: 4-hydroxy-3-{[trans-4-[(1 H-2-methylimidazo[4.5-c]pyrid-1-yl)methylcyclohex-1-yl]carbonyl}indole-1 carboxylic acid dimethyl amide The desired compound is prepared by reaction of a solution in CH$_2$Cl$_2$ of 4-methoxy-3-{[trans-4-[(1H-2-methylimidazo[4.5-c]pyrid-1-yl)methylcyclohex-1-yl]carbonyl}indole-1 carboxylic acid dimethyl amide, prepared as in step 1, with BBr$_3$.

EXAMPLE 13

Preparation of 4-(N,N-dimethylaminocarbonyloxy)-3-{[trans-4-[(1H-2-methylimidazo[4.5-c]pyrid-1-yl)methylcyclohex-1-yl]carbonyl}indole-1 carboxylic acid dimethyl amide hydrochloride The desired compound is prepared by reaction of 4-hydroxy-3-{[trans-4-[(1H-2-methylimidazo[4.5-c]pyrid-1-yl)methylcyclohex-1-yl]carbonyl}indole-1 carboxylic acid dimethyl amide, prepared as in Example 12, with NaH and dimethylcarbamoyl chloride, followed by formation of the hydrochloride salt using HCl/dioxane as described in Example 1, step 8.

EXAMPLE 14

Preparation of 4-chloro-3-{[trans-4-[(1H-2-methylimidazo[4.5-c]pyrid-1-yl)methylcyclohex-1-yl]carbonyl}indol-1 carboxylic acid dimethyl amide hydrochloride The desired compound is prepared according to the method of Example 1, except substituting 4-chloroindole for indole-4-carboxylic acid methyl ester.

18

EXAMPLE 15

Preparation of 1-(2-ethoxyethyl)-6-(4-fluorophenyl)-3-{[trans-4-[(1H-2-methylimidazo[4.5-c]pyrid-1-yl) methylcyclohex-1-yl]carbonyl}indole hydrochloride Step 1: 6-(4-fluorophenyl)-3-{[trans-4-[(1H-2-methylimidazo[4.5-c]pyrid-1-yl)methylcyclohex-1-yl]carbonyl}indole The desired compound is prepared by reaction of 6-(4-fluorophenyl)-3-{[trans-4-[(1H-2-methylimidazo[4.5-c]pyrid-1-yl)methylcyclohex-1-yl]carbonyl}indole-1-carboxylic acid dimethyl amide hydrochloride, prepared as in example 2, with K$_2$CO$_3$ in methanol.

Step 2: 1-(2-ethoxyethyl)-6-(4-fluorophenyl)-3-{[trans-4-[(1H-2-methylimidazo[4.5-c]pyrid-1-yl) methylcyclohex-1-yl]carbonyl}indole hydrochloride The desired compound is prepared by treating a solution in DMF of 6-(4-fluorophenyl)-3-{[trans-4-[(I H-2-methylimidazo[4.5-c]pyrid-1-yl)methylcyclohex-1-yl] carbonyl}indole, prepared as in step 1, with NaH and 2-bromoethyl ethyl ether, followed by isolation of the crude 1-(2-ethoxyethyl)indole derivative and formation of the hydrochloride salt using HCl/dioxane as described in Example 1, step 8.

The compounds represented in Table 3 are prepared using the methods described in Example 15 and WO 93/01813.

TABLE 3

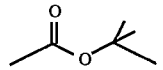

| Example | R$^2$ |
|---|---|
| 16 | —CH$_3$ |
| 17 | 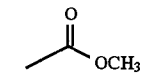 |
| 18 | 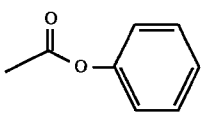 |
| 19 | |

TABLE 3-continued

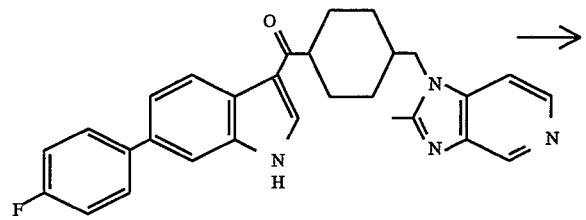

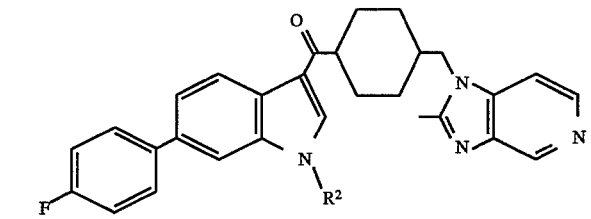

| Example | R² |
|---|---|
| 20 | -CH₂-C(O)NH₂ |
| 21 | -CH₂-C(O)NHCH₃ |
| 22 | -CH₂-C(O)N(CH₃)(C₆H₅) |
| 23 | -CH₂-C(O)N(CH₃)CH₂CH₂N(CH₃)₂ |
| 24 | -CH₂-C(O)NH-CH₂CH₂OH |
| 25 | -CH₂-C(O)NH-CH₂CH₂SO₃H |
| 26 | -CH₂-C(O)NHNH₂ |
| 27 | -CH₂-C(O)NH-CH₂CO₂H |
| 28 | -CH₂CH₂-OH |
| 29 | -CH₂CH₂-NH₂ |
| 30 | -CH₂CH₂-NSO₂CH₃ |
| 31 | -CH₂CH₂-SO₂NH₂ |
| 32 | -CH₂CH₂-CO₂CH₃ |
| 33 | -CH₂CH₂-CO₂CH₂CH₃ |
| 34 | -CH₂CH₂CH₂-CO₂H |
| 35 | -CH₂CH₂-NH-C(O)O-C(CH₃)₃ |
| 36 | -CH₂CH₂-CN |
| 37 | -CH₂CH₂-CO₂H |
| 38 | -CH₂CH₂-C(O)NHCH₃ |
| 39 | -CH₂CH₂-(tetrazolyl) |
| 40 | -SO₂CH₃ |
| 41 | -SO₂CH₂CH₃ |
| 42 | -SO₂C₆H₅ |
| 43 | -SO₂N(CH₃)₂ |

We claim:
1. A compound of formula

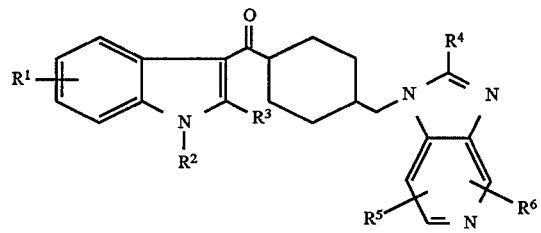

or a pharmaceutically acceptable salt thereof wherein
R¹ is one or more groups independently selected from the group consisting of
(a) hydrogen,
(b) halogen,
(c) hydroxy, (d) cyano,
(e) alkyl of one to six carbon atoms,
(f) alkenyl of two to six carbon atoms,
(g) alkynyl of two to six carbon atoms,
(h) alkoxy of one to six carbon atoms,
(i) alkanoyl of one to seven carbon atoms,
(j) —COOR$^7$, wherein R$^7$ is
 hydrogen,
 alkyl of one to ten carbon atoms, or
 phenylalkyl wherein the alkyl portion is of one to four carbon atoms,
(k) unsubstituted phenyl,
(l) phenyl, substituted with
 alkyl of one to six carbon atoms,
 alkoxy of one to six carbon atoms,
 halogen,
 —NR$^8$R$^9$, where R$^8$ and R$^9$ are independently selected from hydrogen and
  alkyl of one to six carbon atoms,
   or R$^8$ and R$^9$ together with the nitrogen atom to which they are attached form a pyrrolidinyl, piperidinyl, piperazinyl, or morpholinyl ring,
 —COOR$^7$,
 —C(O)NR$^8$R$^9$, or
 —SO$_2$NR$^8$R$^9$,
(m) —C(O)NR$^8$R$^9$,
(n) —OC(O)NR$^8$R$^9$,
(o) —NHC(O)NR$^8$R$^9$,
(p) 2- or 3-furyl,
(q) 2- or 3-thienyl,
(r) 2-, 4-, or 5-thiazolyl,
(s) 2-, 3-, or 4-pyridyl,
(t) 2-, or 4-pyrimidyl,
(u) phenylalkyl in which the alkyl portion is of one to six carbon atoms,
(v) phenylalkyl, in which the alkyl portion is of one to six carbon atoms and the phenyl moiety is substituted with
 halogen,
 alkyl of from one to six carbon atoms, or
 alkoxy of from one to six carbon atoms,
(w) unsubstituted benzoyl,
(x) benzoyl substituted with
 halogen,
 alkyl of from one to six carbon atoms, or
 alkoxy of from one to six carbon atoms,
(y) unsubstituted phenoxy,
(z) phenoxy substituted with
 halogen,
 alkyl of from one to six carbon atoms, or
 alkoxy of from one to six carbon atoms,
(aa) unsubstituted phenylalkyloxy, in which the alkyl portion is of one to six carbon atoms,
(bb) phenylalkyloxy in which the alkyl portion is of one to six carbon atoms and the phenyl moiety is substituted with
 halogen,
 alkyl of from one to six carbon atoms, or
 alkoxy of from one to six carbon atoms,
(cc) unsubstituted phenylalkanoyl, in which the alkanoyl portion is of one to seven carbon atoms, and
(dd) phenylalkanoyl, in which the alkanoyl portion is of one to seven carbon atoms and the phenyl moiety is substituted with;
 halogen,
 alkyl of from one to six carbon atoms, or
 alkoxy of from one to six carbon atoms;

R$^2$ is selected from the group consisting of
(a) hydrogen,
(b) alkyl of one to six carbon atoms;
(c) —(CH$_2$)$_p$COOR$^7$, where p is 0, 1, 2, 3, or 4,
(d) —(CH$_2$)$_q$NR$^8$R$^9$, where q is 2, 3, or 4,
(e) —(CH$_2$)$_p$COR$^7$
(f) —(CH$_2$)$_q$OR$^7$,
(g) —(CH$_2$)$_p$SO$_2$R$^7$,
(h) —(CH$_2$)$_p$SO$_2$NR$^8$R$^9$,
(i) —(CH$_2$)$_p$CONR$^{10}$R$^{11}$, where R$^{10}$ and R$^{11}$ are independently selected from the group consisting of
 hydrogen,
 alkyl of one to six carbon atoms,
 —(CH$_2$)$_r$COOR$^7$, where r is 1, 2, 3, or 4,
 —(CH$_2$)$_r$NR$^8$R$^9$,
 (CH$_2$)$_r$OR$^7$,
 —(CH$_2$)$_r$SO$_2$R$^7$, and
 —(CH$_2$)$_r$SO$_2$NR$^8$R$^9$,
 or R$^{10}$ and R$^{11}$ taken together define a pyrrolidine, morpholine, or thiomorpholine ring,
(j) —(CH$_2$)$_p$CN,
(k) —(CH$_2$)$_p$-1H-tetrazol-5-yl,
(l) —CONHNH$_2$,
(m) unsubstituted phenylalkyl wherein the alkyl portion is of one to four carbon atoms, and
(n) phenylakyl wherein the alkyl portion is of one to four carbon atoms and the phenyl moiety is substituted with
 halogen,
 alkyl of from one to six carbon atoms, or
 alkoxy of from one to six carbon atoms;

R$^3$ is selected from the group consisting of hydrogen and alkyl of one to six carbon atoms;

R$^4$ is selected from the group consisting of
(a) alkyl of one to six carbon atoms,
(b) alkenyl of two to six carbon atoms,
(c) alkynyl of two to six carbon atoms,
(d) alkoxy of one to six carbon atoms,
(e) alkylthio of one to six carbon atoms,
(f) alkoxyalkyl in which the alkoxy and alkyl portions are independently of one to six carbon atoms,
(g) alkylthioalkyl in which the alkyl portions each independently of one to six carbon atoms,
(h) haloalkyl of one to six carbon atoms,
(i) unsubstituted phenylalkyl wherein the alkyl portion is of one to six carbon atoms,
(j) phenylalkyl wherein the alkyl portion is of one to six carbon atoms and the phenyl is substituted with
 alkyl of one to six carbon atoms,
 haloalkyl of one to six carbon atoms,
 alkoxy of one to six carbon atoms,
 hydroxy, or
 halogen,
(k) cycloalkyl of three to eight carbon atoms,
(l) unsubstituted thiophenyl, and
(m) thiophenyl substituted with
 alkyl of one to six carbon atoms,
 haloalkyl of one to six carbon atoms,
 alkoxy of one to six carbon atoms, hydroxy, or
halogen; and $R^5$ and $R^6$ are independently selected from the group consisting of
hydrogen,
alkyl of one to six carbon atoms,
halogen,
haloalkyl, and
alkoxy of one to six carbon atoms.

2. A compound or pharmaceutically acceptable salt thereof as defined by claim 1 wherein $R^1$ is one or more groups independently selected from the group consisting of
hydrogen,
halogen,
alkyl of one to six carbon atoms,
alkynyl of two to four carbon atoms,
alkoxy of one to six carbon atoms,
unsubstituted phenyl,
phenyl, substituted with
  alkyl of one to six carbon atoms,
  alkoxy of one to six carbon atoms,
  halogen,
—COOR$^7$, wherein $R^7$ is hydrogen, alkyl of one to ten carbon atoms, or phenylalkyl wherein the alkyl portion is of one to four carbon atoms,
—C(O)NR$^8$R$^9$,
—OC(O)NR$^8$R$^9$,
2- or 3-furyl, and
2- or 3-thienyl;

$R^3$, $R^5$ and $R^6$ are hydrogen; and $R^4$ is alkyl of one to six carbon atoms.

3. A compound or pharmaceutically acceptable salt thereof as defined by claim 2 wherein $R^2$ is selected from the group consisting of
—CONR$^{10}$R$^{11}$, where $R^{10}$ and $R^{11}$ are independently selected from the group consisting of
hydrogen and
alkyl of one to six carbon atoms, and
—(CH$_2$)$_q$OR$^7$, wherein q is 2, 3, or 4, and $R^7$ is alkyl of one to four carbon atoms.

4. A compound or pharmaceutically acceptable salt thereof as defined by claim 1 selected from the group consisting of 3-{[trans-4-[(1H-2-methylimidazo[4.5-c]pyrid-1-yl) methylcyclohex-1-yl]carbonyl}indole-1,4-dicarboxylic acid 1-dimethyl amide 4-methyl ester hydrochloride, 6-(4-fluorophenyl)-3-{[trans-4-[(1H-2-methylimidazo [4.5-c]pyrid-1-yl)methylcyclohex-1-yl] carbonyl}indole-1 carboxylic acid dimethyl amide hydrochloride, 6-(4-fluorophenoxy)-3-{[trans-4-[(1H-2-methylimidazo [4.5-c]pyrid-1-yl)methylcyclohex-1-yl] carbonyl}indole-1 carboxylic acid dimethyl amide hydrochloride, 6-phenylmethyl-3-{[trans-4-[(1H-2-methylimidazo[4.5-c]pyrid-1-yl)methylcyclohex-1-yl]carbonyl}indole-1 carboxylic acid dimethyl amide hydrochloride, 6-(4-methoxyphenyl)-3-{[trans-4-[(1H-2-methylimidazo [4.5-c]pyrid-1-yl)methylcyclohex-1-yl] carbonyl}indole-1 carboxylic acid dimethyl amide hydrochloride, 6-(pyrid-3-yl)-3-{[trans-4-[(1H-2-methylimidazo[4,5-c] pyrid-1-yl)methylcyclohex-1-yl]carbonyl}indole-1 carboxylic acid dimethyl amide hydrochloride, 5-methoxy-3-{[trans-4-[(1H-2-methylimidazo[4.5-c] pyrid-1-yl)methylcyclohex-1-yl]carbonyl}indole-1 carboxylic acid dimethyl amide hydrochloride, 4-methyl-3-{[trans-4-[(1H-2-methylimidazo[4.5-c]pyrid-1-yl)methylcyclohex-1-yl]carbonyl}indole-1 carboxylic acid dimethyl amide hydrochloride, 4-ethynyl-3-{[trans-4-[(1H-2-methylimidazo[4.5-c] pyrid-1-yl) methylcyclohex-1-yl]carbonyl}indole-1 carboxylic acid dimethyl amide hydrochloride, 4-(fur-2-yl)-3-{[trans-4-[(1H-2-methylimidazo[4.5-c] pyrid-1-yl)methylcyclohex-1-yl]carbonyl}indole-1 carboxylic acid dimethyl amide hydrochloride, 4-(thien-2-yl)-3-{[trans-4-[(1H-2-methylimidazo[4.5-c] pyrid-1-yl)methylcyclohex-1-yl]carbonyl}indole-1 carboxylic acid dimethyl amide hydrochloride, 4-hydroxy-3-{[trans-4-[(1H-2-methylimidazo[4.5-c] pyrid-1-yl)methylcyclohex-1-yl]carbonyl}indole-1 carboxylic acid dimethyl amide hydrochloride, 4-(N,N-dimethylaminocarbonyloxy)-3-{[trans-4-[(1H-2-methylimidazo[4.5-c]pyrid-1-yl)methylcyclohex-1-yl] carbonyl}indole-1 carboxylic acid dimethyl amide hydrochloride, 4-chloro-3-{[trans-4-[(1H-2-methylimidazo[4.5-c]pyrid-1-yl)methylcyclohex-1-yl]carbonyl}indole-1 carboxylic acid dimethyl amide hydrochloride, and 1-(2-ethoxyethyl)-6-(4-fluorophenyl)-3-{[trans-4-[(1H-2-methylimidazo[4.5-c]pyrid-1-yl)methylcyclohex-1-yl]carbonyl}indole hydrochloride.

5. A compound or pharmaceutically acceptable salt thereof as defined by claim 1 selected from the group consisting of:

3-{[trans-4-[(1H-2-methylimidazo[4.5-c]pyrid-1-yl) methylcyclohex-1 -yl]carbonyl}indole-1,4-dicarboxylic acid 1-dimethyl amide 4-methyl ester hydrochloride.

6. A pharmaceutical composition useful for inhibiting PAF in a mammal in need of such treatment comprising a PAF-inhibitive effective amount of a compound as defined by claim 1 in combination with a pharmaceutically acceptable carrier.

7. A method of treating PAF mediated disorders comprising administering to a mammal in need of such treatment a therapeutically effective amount of a compound as defined by claim 1.

\* \* \* \* \*

UNITED STATES PATENT AND TRADEMARK OFFICE
CERTIFICATE OF CORRECTION

PATENT NO. : 5,643,922
DATED : July 1, 1997
INVENTOR(S) : Sheppard et al.

It is certified that error appears in the above-identified patent and that said Letters Patent is hereby corrected as shown below:

Column 24, line 8, change "[4,5-c]" to --[4.5-c]--.

Signed and Sealed this

Twenty-eighth Day of October, 1997

*Attest:*

BRUCE LEHMAN

*Attesting Officer*     *Commissioner of Patents and Trademarks*